US006255559B1

(12) United States Patent
Cheah

(10) Patent No.: US 6,255,559 B1
(45) Date of Patent: Jul. 3, 2001

(54) METHODS FOR PRODUCING GENETICALLY MODIFIED PLANTS, GENETICALLY MODIFIED PLANTS, PLANT MATERIALS AND PLANT PRODUCTS PRODUCED THEREBY

(75) Inventor: Kheng Tuan Cheah, Auckland (NZ)

(73) Assignees: Genesis Research & Development Corp. Ltd.; Fletcher Challenge Forests Ltd., both of Auckland (NZ)

( * ) Notice: Subject to any disclaimer, the term of this patent is extended or adjusted under 35 U.S.C. 154(b) by 0 days.

(21) Appl. No.: 09/153,320

(22) Filed: Sep. 15, 1998

(51) Int. Cl.⁷ ............................... A01H 4/00; A01H 7/00; C12N 15/00; C12N 15/82; C12N 15/84
(52) U.S. Cl. .................... 800/278; 800/279; 800/281; 800/283; 800/284; 800/290; 800/288; 800/289; 800/300; 800/302; 800/303; 800/319; 800/323; 800/294; 435/418; 435/419; 435/422; 435/430; 435/468; 435/469
(58) Field of Search .................. 435/468, 469, 435/410, 413, 418, 419, 430, 422; 800/278, 290, 295, 298, 300, 319, 279, 281, 283, 303, 284, 280, 302, 288, 294, 289, 323

(56) References Cited

FOREIGN PATENT DOCUMENTS

| 9625504 | 8/1996 | (WO) | C12N/15/82 |
| 00625 | 9/1997 | (WO) | C12N/15/82 |

OTHER PUBLICATIONS

Walter et al. FRI Bull. 1997, 203 (IUFRO '97, Genetics of Radiata Pine), 319–332 (Abstract), 1997.*
McGranahan et al. Bio/Technology. 1988. vol. 6: 800–804.*
Tzfira et al. Plant Cell Reports. 1996. vol. 16: 26–31.*
De Oliverira et al. Plant Cell Reports. 1997. vol. 16: 299–303.*
E. Pérez–Molphe–Balch, et al., "Regeneration of Transgenic Plants of Mexican Lime From *Agrobacterium Rhizogenes*–Transformed Tissues," *Plant Cell Reports,* vol. 17, pp. 591–596 (1998).

Y. Nakamura, et al., "Agrobacterium–Mediated Transformation and Plant Regeneration From Hypocotyl Segments of Japanese Persimmon (*Diospyros kaki Thunb*)," *Plant Cell Reports,* vol. 17, pp. 435–440 (1998).
Tzvi Tzfira, et al., "Transformation and Regeneration of Transgenic Aspen Plants Via Shoot Formation From Stem Explants," *Physiologia Plantarum,* vol. 99, pp. 554–561 (1997).
Kei–ichiro Ueno, et al., "Genetic Transformation of Rhododendron by *Agrobacterium Tumefaciens*," *Plant Cell Reports,* vol. 16, pp. 38–40 (1996).
Dong–Ill Shin, et al., "Transgenic Larch Expressing Genes for Herbicide and Insect Resistance," *Canadian Journal of Forest Research,* vol. 24, pp. 2059–2067 (1994).
J. Kaneyoshi (Hiramatsu), et al., "A Simple and Efficient Gene Transfer System of Trifoliate Orange (*Poncirus trifoliate* Raf.)," *Plant Cell Reports,* vol. 13, pp. 541–545 (1994).
K.V. Mullins et al., Regeneration and transformation of *Eucalyptus camaldulensis, Plant Cell Reports* 16: 787–791, 1997.
J.J. Le Roux et al., Micropropagation and tissue culture of Eucalyptus—a review, *Tree Physiology* 9, 435–477, 1991.
Eucalyptus Transformation, Excerpt from *1997 Biological Sciences Symposium,* 1313–1326, 1997.

* cited by examiner

Primary Examiner—David T. Fox
Assistant Examiner—O. M. F. Zaghmout
(74) Attorney, Agent, or Firm—Ann W. Speckman; Jim Klaniecki

(57) ABSTRACT

Methods for producing genetically modified plants, particularly woody plants, and most particularly plants of the Eucalyptus and Pinus species, involve transformation of target plant material with a desired genetic construct and regeneration of the transformed plant material using an adventitious shoot bud system. The methods provide a high transformation efficiency and substantially reduce the duration of the transformation and regeneration protocols. Stem segments of a target plant are transformed using Agrobacterium-mediated techniques, and adventitious shoot buds are regenerated from the Agrobacterium-infected stem segments. Preferred culture media, including selection media, and improved plant culture techniques are disclosed.

16 Claims, No Drawings

METHODS FOR PRODUCING GENETICALLY MODIFIED PLANTS, GENETICALLY MODIFIED PLANTS, PLANT MATERIALS AND PLANT PRODUCTS PRODUCED THEREBY

TECHNICAL FIELD OF THE INVENTION

This invention relates to methods for producing genetically modified plants, particularly woody plants, and most particularly plants of the Eucalyptus and Pinus species, as well as plants, plant materials and plant products produced by or from such genetic modification. This invention relates, more specifically, to techniques for producing genetically modified plants, including transgenic woody plants and interspecies hybrid woody plants, particularly of the Eucalyptus and Pinus species.

BACKGROUND OF THE INVENTION

Recent advances in plant genetic engineering have made possible the transfer of DNA into plants, including commercially important forestry tree species. The application of genetic engineering to commercially important forestry varieties provides opportunities to incorporate new or improved traits of commercial interest, such as disease resistance, male sterility, increased productivity, rooting ability, wood quality, and others, in forestry varieties.

Commercial scale planting stocks of forestry varieties are generally produced directly from seed or from rooted cuttings. In both of these production systems, traditional plant-breeding techniques are used to produce superior planting stock. The application of genetic engineering techniques to stably incorporate homologous and/or heterologous genetic material into plants offers the potential of improved planting stocks compared to those developed using traditional breeding techniques.

The overall efficiency of techniques for genetically modifying plants depends upon the efficiency of the transformation technique(s) used to stably incorporate the homologous and/or heterologous genetic material into plant cells or tissues, and the regeneration technique(s) used to produce viable plants from transformed cells. In general, the efficiency of transformation and regeneration techniques adapted for genetically modifying forestry plants, such as plants of the Eucalyptus species, is low.

Publications report the successful transfer of DNA into commercial varieties of tree species, including Eucalyptus. 1997 Biological Sciences Symposium, "Prospects For Eucalyptus Tranformation," TAPPI Press, pp.313–326. Genetic transformation has generally been achieved through Agrobacterium-mediated transformation. Transformation techniques have been demonstrated using reporter genes such as GUS ((-glucuronidase), nptli and cat (chloramphenical acetyl transferase). A reproducible and reliable tissue culture regeneration system is required for regenerating plants from transformed cells. Regeneration systems developed for use with forestry varieties have generally demonstrated very low levels of reproducibility and efficiency. Regeneration is generally the limiting factor in the production of transgenic forestry species.

Techniques for plant tissue culture have been developed and used extensively for micropropagation of various Eucalyptus species. J. J. LeRoux and J. Van Staden, "Micropropagation and tissue culture of Eucalyptus—a review," Tree Physiology 9, 435–477, 1991. Techniques used for micropropagation generally involve axillary bud multiplication. The axillary bud is induced form the leaf axils of stem segments, the bud is allowed to elongate into a shoot, and it is then allowed to multiply in the same manner, producing more axillary shoots. When sufficient copies of a clone are produced, the shoots are rooted and then transplanted. This system has been widely used for commercial production of clones for reforestation because it reliably produces stably cloned propagules that are true to type.

Although the axillary bud multiplication system is well developed, it is not a preferred regeneration system for regenerating genetically modified plants. Transgenic plants produced using axillary bud multiplication regeneration techniques are often chimeric because the axillary buds are generated from preformed buds that may carry a mixture of transformed and non-transformed cells. Only portions of transgenic plants produced from chimeric tissues are transformed and carry the introduced genetic material.

Applicants are aware of two published protocols for regeneration of Eucalyptus. In a protocol published in Plant Cell Reports 13:473–476, 1994, an organogenesis pathway using leaf explants was described. In a protocol published in Suid-Afrikaanse Bobboutydskrif 157:59–65, 1991, a somatic embryogenesis pathway using leaf explants was described. These reported systems demonstrated a low efficiency and, additionally required an impractically long time period for the regeneration process. The long duration (six months) of the regeneration process is not commercially feasible. Furthermore, neither of these systems was successfully reproduced by applicants.

The success and efficiency of methods for producing genetically modified plants thus depends on the selection and optimization of a tissue culture regeneration system that provides de novo origination of plant material from transformed cells, and development of the genetically modified plant material to produce a genetically modified plant. Techniques developed to date for genetically modifying forestry species such as Eucalyptus generally demonstrate low reproducibility of the regeneration protocol, long duration of regeneration, low efficiency of plant regeneration (0–5%), and low transformation efficiency. The present invention is directed to improved methods for producing genetically modified plants, particularly forestry species, and most particularly plants of the Eucalyptus and Pinus species.

SUMMARY OF THE INVENTION

The present invention involves methods for producing genetically modified plant material, particularly woody plant material of the Eucalyptus or Pinus species. The methods of the present invention involve introduction of genetic material using transformation techniques. Agrobacterium-mediated transformation techniques whereby one or more genetic construct(s) comprising a reporter gene and the genetic material desired to be introduced is transformed into an Agrobacterium strain using well known techniques.

Preferred tissue explants of the target plant comprise stem segments from micropropagated shoot cultures. The target plant stem segments may be pretreated in a multiplication medium and then transferred to a shoot elongation medium to promote formation of mature shoots. Nodes may be excised from the target plant stem segments and leaves from the stem segments and/or selected nodes of the shoot explants are preferably removed. The stem segments and/or nodes may be additionally wounded, such as by cutting. The stem segments and/or nodes may then be incubated with a transformed Agrobacterium culture to inoculate the target plant explants with the desired genetic material. Following inoculation, regeneration of adventitious shoot buds from the Agrobacterium infected stem segments is promoted in tissue culture using a combination of regeneration agents. The system of the present invention is advantageous for producing genetically modified plants because it employs transformation and regeneration techniques that provide de novo shoot origination from transformed cells.

Following a suitable period for adventitious shoot bud formation, putative transformed adventitious shoots may be excised from the stem segments. Selection techniques may then be used to identify successfully transformed adventitious shoot buds. The selection technique may vary, depending upon the reporter construct used. According to preferred embodiments, the reporter construct introduced to the Agrobacterium and, then, the explants, includes an antibiotic-resistance gene. In this system, suitable selection agents comprise antibiotic agents. A two stage selection technique is preferably employed, whereby the adventitious shoot buds are exposed to a first selection medium having a first concentration of the selection agent, preferably an antibiotic, and the surviving adventitious buds are then are exposed to a second selection medium having a second concentration of the selection agent, the second antibiotic concentration being greater than the first antibiotic concentration. This two stage selection technique substantially eliminates the presence of chimeric shoots in the selected adventitious shoot buds.

Following selection of transformed adventitious shoots, the transformed adventitious shoot buds are transferred to a rooting medium and roots are generated using techniques that are well known in the art. Rooted shoots, or plantlets, may then be transferred to planting medium and planted to complete the transformation and regeneration procedure. The plantlets include the genetic material introduced using the genetic construct. Genetically modified plantlets may be grown to genetically modified mature plants. The products obtained from genetically modified mature plants, such as timber, wood pulp, fuel wood, and the like, also contain the genetic modification.

The transformation and regeneration methods of the present invention are reproducible and substantially reduce the duration of transformation and regeneration of genetically modified plant materials compared to methods previously reported for forestry plant species. Applied to the Eucalyptus species, methods of the present invention reduce the time required for transformation and regeneration from six months or more to about ten to fifteen weeks. This reduction is substantial. The methods of the present invention are suitable for commercial production of genetically modified plants, including forestry species such as Eucalyptus and Pinus.

The methods of the present invention for producing genetically modified plants and plant materials are especially suitable for use with forestry species, particularly Eucalyptus and Pinus species. These methods may provide the introduction of new genes, additional copies of existent genes, or non-coding portions of a genome, into selected clones with little disturbance of the plant's genome. Genetic material that produces desirable traits, such as insect tolerance, disease resistance, herbicide tolerance, male sterility, rooting ability, cold tolerance, drought tolerance, salinity tolerance, and modification of wood properties and growth rates and properties, and the like, may be introduced. The genetic material introduced may be homologous or heterologous to the genome of the target plant.

The present invention also contemplates plants, plant materials, and plant products derived from genetically modified plants produced according to methods of the present invention. Plants include mature and immature plants grown from plantlets produced according to methods of the present invention, as well as plants propagated using materials from such plants. Plant materials include plant cells or tissues such as seeds, flowers, bark, stems, etc. of all such plants. Plant products include any materials derived from plant materials, such as wood products, pulp products, and the like.

DESCRIPTION OF PREFERRED EMBODIMENTS

Using the methods and materials of the present invention, the genome of a target plant may be modified by incorporating homologous or heterologous genetic material. Additional copies of genes encoding certain polypeptides, or finctional portions of certain polypeptides, such as enzymes involved in a biosynthetic pathway, may be introduced into a target plant using the methods of the present invention to increase the level of a polypeptide of interest. Similarly, a reduction in the level of a polypeptide of interest in a target plant may be achieved by transforming the target plant with antisense copies of genes encoding the polypeptide of interest, or a functional portion of the polypeptide of interest. Additionally, the number of copies of genes encoding different polypeptides, such as enzymes in a biosynthetic pathway, may be manipulated to modify the relative amount of each polypeptide synthesized, leading to the formation of an end product having a modified composition. Non-coding portions of polynucleotides, such as regulatory polynucleotides and polynucleotides encoding regulatory factors, such as transcription factors, and/or functional portions of transcription factors, and/or antisense copies of such regulatory factors, may also be introduced to target plant material to modulate the expression of certain polypeptides. These materials are exemplary of the types of genetic material suitable for modifying the genome of target plant material. Numerous other materials may also be introduced.

The methods of the present invention preferably employ shoot cultures of the target plant material as a starting material. Micropropagated shoot cultures may be generated by surface sterilizing young shoots from field grown juvenile and mature stage target plants in a sterilization medium, rinsing the sterilized shoots, and then exposing them to a multiplication or elongation medium. Suitable sterilization media, such as 0.01% mercuric chloride solution, are known, and repeated rinsing may be performed with sterile, distilled water. Alternatively, micropropagated shoot cultures may be obtained from forestry companies.

According to preferred embodiments, in vitro micropropagated shoot cultures are grown for a period of from one week to several weeks, preferably three weeks, on a multiplication medium. A preferred multiplication medium comprises full strength MS (Murashige and Skoog) medium (Sigma M5519), sucrose, Benzylaminopurine (BA), and Naphthalene Acidic Acid (NAA). The multiplication medium preferably comprises sucrose at a concentration of 30 g/l, BA at a concentration of 0.1 mg/l, and NAA at a concentration of 0.01 mg/l in full strength MS medium.

The shoot cultures may then preferably be transferred to a shoot elongation medium. The shoot elongation medium additionally comprises a plant growth promoter, such as gibberellic acid, at a concentration of about 1 mg/l. Shoot cultures are preferably exposed to the shoot elongation medium for at least three weeks, more preferably for four to six weeks. Shoot cultures are preferably subcultured to fresh medium every two to four weeks, and are preferably transferred to fresh medium about two to three weeks before transformation. Shoots of the target plant material are preferably allowed to grow to a size of from 1 to 8 cm in length, more preferably from about 3 to 4 cm in length, before they are transformed to incorporate the desired genetic material.

Unless otherwise noted, in vitro cell culture conditions preferably include a 16 hour photoperiod using cool white fluorescent lighting and temperatures of about 20° C. Cultures are preferably grown in petri dishes, with multiple shoots per petri dish, and with the shoots arranged horizontally.

The "genetic material" transformed into the target plant material includes one or more genetic construct(s) comprising one or more polynucleotide(s) desired to be introduced to the target plant material, and a reporter construct. Genetic constructs introduced into the target plant material may comprise genetic material that is homologous and/or heterologous to the target plant material, and may include polynucleotides encoding a polypeptide, a functional portion of a polypeptide, a polypeptide encoding a regulatory factor, such as a transcription factor, non-coding polynucleotides such as regulatory polynucleotides, and antisense polynucleotides that inhibit expression of a specified polypeptide. The genetic construct is preferably functional in the target plant.

According to one embodiment, the genetic constructs used in connection with the present invention include an open reading frame coding for at least a functional portion of a polypeptide of interest in the target plant material. A polypeptide of interest may be a structural or functional polypeptide, or a regulatory polypeptide such as a transcription factor. As used herein, the "functional portion" of a polypeptide is that portion which contains the active site essential for affecting the metabolic step, i.e. the portion of the molecule that is capable of binding one or more reactants or is capable of improving or regulating the rate of reaction. The active site may be made up of separate portions present on one or more polypeptide chains and will generally exhibit high substrate specificity.

A target plant may be transformed with more than one genetic construct of the present invention, thereby modulating a biosynthetic pathway for the activity of more than one polypeptide, affecting an activity in more than one tissue or affecting an activity at more than one expression time. Similarly, a genetic construct may be assembled containing more than one open reading frame coding for a polypeptide or more than one non-coding region of a gene.

The word "polynucleotide(s)," as used herein, means a polymeric collection of nucleotides and includes DNA and corresponding RNA molecules, both sense and anti- sense strands, and comprehends cDNA, genomic DNA and recombinant DNA, as well as wholly or partially synthesized polynucleotides. A polynucleotide may be an entire gene, or any portion thereof. Operable anti-sense polynucleotides may comprise a fragment of the corresponding polynucleotide, and the definition of "polynucleotide" therefore includes all such operable anti-sense fragments. Identification of genomic DNA and heterologous species DNAs can be accomplished by standard DNA/DNA hybridization techniques, under appropriately stringent conditions, using all or part of a cDNA sequence as a probe to screen an appropriate library. Alternatively, PCR techniques using oligonucleotide primers that are designed based on known genomic DNA, cDNA and protein sequences can be used to amplify and identify genomic and cDNA sequences. Synthetic DNAs corresponding to the identified sequences and variants may be produced by conventional synthetic methods. All of the polynucleotides described herein are isolated and purified, as those terms are commonly used in the art. A polynucleotide of interest, as used herein, is a polynucleotide that is homologous or heterologous to the genome of the target plant and alters the genome of the target plant.

As used herein, the term "polypeptide" encompasses amino acid chains of any length, including full length proteins, wherein amino acid residues are linked by covalent peptide bonds.

When the genetic construct comprises a coding portion of a polynucleotide, the genetic construct further comprises a gene promoter sequence and a gene termination sequence operably linked to the polynucleotide to be transcribed. The gene promoter sequence is generally positioned at the 5' end of the polynucleotide to be transcribed, and is employed to initiate transcription of the polynucleotide. Promoter sequences are generally found in the 5' non-coding region of a gene but they may exist in introns or in the coding region. When the construct includes an open reading frame in a sense orientation, the gene promoter sequence also initiates translation of the open reading frame. For genetic constructs comprising either an open reading frame in an antisense orientation or a non-coding region, the gene promoter sequence may comprise a transcription initiation site having an RNA polymerase binding site.

A variety of gene promoter sequences which may be usefully employed in the genetic constructs of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of a polypeptide in all parts of the plant. Use of a tissue specific promoter will result in production of the desired sense or antisense RNA only in the tissue of interest. With genetic constructs employing inducible gene promoter sequences, the rate of RNA polymerase binding and initiation may be modulated by external stimuli, such as light, heat, anaerobic stress, alteration in nutrient conditions and the like. Temporally regulated promoters may be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, such as Eucalyptus or Pinus, are used. Other examples of gene promoters which may be usefully employed in the present invention include mannopine synthase (mas), octopine synthase (ocs) and those reviewed by Chua et al. (Science, 244:174–181, 1989).

The gene termination sequence, which is located 3' to the DNA sequence to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original polypeptide gene, or from the target species being transformed.

The genetic constructs of the present invention also comprise a reporter gene or a selection marker that is effective in target plant cells to permit the detection of transformed cells containing the genetic construct. Such reporter genes and selection markers, which are well known in the art, typically confer resistance to one or more toxins. A chimeric gene that expresses β-D-glucuronidase (GUS) in transformed plant tissues but not in bacterial cells is a preferred selection marker for use in methods of the present invention. The binary vector pKIWI 105, constructed as described by Janssen and Gardner in Plant Molecular Biology 14: 61–72, 1989, is an especially preferred selection marker. Plant material expressing GUS is resistant to antibiotics such as kanamycin. Another suitable marker is the NPTII gene, whose expression results in resistance to kanamycin or hygromycin, antibiotics which are generally toxic to plant cells at a moderate concentration. Rogers et al. in Methods for Plant Molecular Biology, A. Weissbach and H. Weissbach, eds., Academic Press Inc., San Diego, Calif. (1988). Alternatively, the presence of the desired construct in transformed cells may be determined by means of other techniques that are well known in the art, such as Southern and Western blots.

Techniques for operatively linking the components of the genetic constructs used to transform target plant materials are well known in the art and include the use of synthetic linkers containing one or more restriction endonuclease sites as described, for example, by Maniatis et al., (Molecular Cloning: A Laboratory Manual, Cold Spring Harbor Laboratories, Cold Spring Harbor, N.Y., 1989). Genetic constructs used in methods of the present invention may be linked to a vector having at least one replication system, for example, E. coli, whereby after each manipulation, the resulting construct can be cloned and sequenced and the correctness of the manipulation determined.

For applications where amplification of a polypeptide is desired, an open reading encoding the polypeptide of interest, or a polynucleotide encoding a regulatory factor that modulates expression of the polypeptide of interest, may be inserted in the genetic construct in a sense orientation, such that transformation of a target plant with the genetic construct will produce an increase in the number of copies of the gene or an increase in the expression of the gene and, consequently, an increase in the amount of the polypeptide. When down-regulation of a polypeptide is desired, an open reading frame encoding the polypeptide of interest may be inserted in the genetic construct in an antisense orientation, such that the RNA produced by transcription of the polynucleotide is complementary to the endogenous mRNA sequence. This, in turn, will result in a decrease in the number of copies of the gene and therefore a decrease in the amount of enzyme. Alternatively, down-regulation may be achieved by inserting a polynucleotide encoding a regulatory factor that inhibits expression of the polynucleotide encoding the polypeptide of interest.

In another embodiment, the genetic construct used to transform the target plant material may comprise a nucleotide sequence including a non-coding region of a gene coding for a polynucleotide of interest, or a nucleotide sequence complementary to such a non-coding region. As used herein the term "non-coding region" includes both transcribed sequences which are not translated, and non-transcribed sequences within about 2000 base pairs 5' or 3' of the translated sequences or open reading frames. Examples of non-coding regions which may be usefully employed in the inventive constructs include introns and 5'-non-coding leader sequences. Transformation of a target plant with such a genetic construct may lead to a reduction in the amount of a selected polypeptide synthesized by the plant by the process of cosuppression, in a manner similar to that discussed, for example, by Napoli et al. (Plant Cell 2:279–290, 1990) and de Carvalho Niebel et al. (Plant Cell 7:347–358, 1995).

Genetic constructs may be used to transform a variety of plants using the methods of the present invention, including monocotyledonous (e.g. grasses, corn, grains, oat, wheat and barley), dicotyledonous (e.g. Arabidopsis, tobacco, legumes, alfalfa, oaks, Eucalyptus, maple), and Gymnosperms (e.g. Scots pine (Aronen, Finnish Forest Res. Papers, vol. 595, 1996), white spruce (Ellis et al., Biotechnology 11:94–92, 1993), larch (Huang et al., In vitro Cell 27:201–207, 1991). In preferred embodiments, the genetic constructs are employed to transform "woody plants," which are herein defined as a tree or shrub whose stem lives for a number of years and increases in diameter each year by the addition of woody tissue. The target plant is preferably selected from the group consisting of the Eucalyptus and Pinus species, most preferably from the group consisting of *Eucalyptus grandis* and *Pinus radiata*.

Techniques for stably incorporating genetic constructs into the genome of target plants are well known in the art and include Agrobactenum-mediated introduction, electroporation, protoplast fusion, injection into reproductive organs, injection into immature embryos, high velocity projectile introduction, and the like. The choice of technique will depend upon the target plant to be transformed. For example, dicotyledonous plants and certain monocots and gymnosperms may be transformed by Agrobacterium Ti plasmid technology as described, for example by Bevan (Nucl. Acid Res. 12:8711–8721, 1984). Targets for the introduction of the genetic constructs of the present invention include tissues, such as leaf tissue, disseminated cells, protoplasts, seeds, embryos, meristematic regions, cotyledons, hypocotyls, and the like. Preferred target plant materials for transformation according to methods of the present invention include in vitro micropropagated shoot cultures prepared as described above.

Transfer of one or more genetic constructs into target plant shoots is preferably accomplished using Agrobacterium-mediated transformation techniques. Numerous 7; Agrobacterium strains are suitable and are commercially available. *Agrobacterium tumefaciens* strain AGL1 (Bio-Technology (9:963–967, 1991) is available and is a preferred Agrobacterium strain. Methods for transforming a population of the Agrobacterium strain with a genetic construct are well known. The free thaw method described in An G., Elbert P., Mitra A., and Ha S., "Binary Vectors," in: Gelvin SB, Schilperoorth RA (eds), Plant Molecular Biology Manual, pp. A3/1–A3119, Dordrecht: Kluwer Academic Publishers, 1988, is a preferred method for transforming the Agrobacterium culture with the genetic construct of interest.

According to preferred embodiments, colonies of Agrobacterium carrying the genetic construct of interest are prepared for inoculation of the target plant material according to the following techniques. Agrobacterium colonies are grown on a growth medium such as YEP medium comprising yeast, peptone and sodium chloride. According to especially preferred embodiments, the growth medium comprises yeast at a concentration of 20 g/l, peptone at a concentration of 20 g/l and sodium chloride at a concentration of 10 g/l. A single colony from the plate may be selected and grown in a culture medium comprising a selection agent for the selection marker. Suitable selection agents comprise, for example, antibiotics. According to an especially preferred embodiment using an Agrobacterium culture transformed with a genetic construct comprising a chimeric GUS gene, the selection agent is kanamycin. The selected Agrobacterium colony is preferably grown in YEP medium comprising kanamycin and rifampicin. Preferred medium comprises 100 mg/l kanamycin and 50 mg/l rifampicin. Cultures may be incubated at 29° C. with vigorous shaking for several hours. The culture may then be centrifuged, washed, and resuspended in medium such as an MS medium comprising acetosyringone at a concentration of 50M. The inoculum is preferably adjusted to an $OD_{600}$ of about 0.15, and cultured on a shaker for several hours at 29° C. before inoculation.

Mature shoots of the target plant material prepared as described above are selected for transformation. Stem segments from each node are excised. Stem segments from the second and third nodes are preferred for use in methods of the present invention. All leaves are preferably peeled from the stems, and additional wounding may be inflicted, for example, by light longitudinal cutting of both sides of the stem with a scalpel blade. The selected stem segments, preferably including the second and third nodes, are inoculated with the Agrobacterium culture prepared as described above.

Inoculation of stem segments with the Agrobacterium suspension takes place under conditions that optimize infection of the stem segments. An incubation may be continued for at least about twenty minutes, more preferably about thirty minutes, on a shaker at a temperature of about 20° C. Alternative suitable techniques are well known. After incubation, excess suspension is removed and stem segments are transferred to a co-cultivation medium. Suitable co-cultivation medium comprises MS medium with about 0.4% glucose. Co-cultivation preferably takes place with the explant stem segments placed horizontally on the surface of the medium during a three day co-cultivation period.

Following the co-cultivation period, stem segments are removed from the medium and washed. A preferred washing medium comprises MS medium comprising timentin, preferably at a concentration of 250 mg/l. Stem segments are then cultured, preferably vertically, in a first selection medium. The first selection medium preferably comprises MS medium, a carbon source, a cytokinin and/or an auxin, timentin and a selection agent. Suitable carbon sources include sucrose and /or glucose at a concentration of from about 5 to 100 g/l. Sucrose at a concentration of more than about 2%, and preferably about 3%, is a preferred carbon source. Suitable cytokinins include BA, Dimethylallylaminopurine (2iP), Kinetin (K) and Zeatin (Z) at a concentration of from about 0.1 to 10 mg/l. Suitable auxins include NAA, Indoleacetic acid (IAA), Indolebutyric acid (IBA), and 2,4-dichlorophenoxiyacetic acid (2,4-D) at a concentration of about 0.001 to 1 mg/l. The preferred concentration of timentin is about 250 mg/l. The preferred selection agent is kanamycin at a concentration of about 50 mg/l. The choice and concentration of the selection agent will depend upon the selection marker introduced in the genetic construct. The pH of the first selection medium is preferably adjusted to about 5 to 6. Stem segments are subcultured in fresh medium each week for at least about 4 weeks until adventitious buds are produced from the stem segments.

Putative transformed adventitious shoots are excised from the stem segments and transferred to shoot elongation medium or a second selection medium. A preferred shoot elongation medium comprises full strength MS medium, sucrose at a concentration of about 30 g/l, BA at a concentration of about 0.1 mg/l, NAA at a concentration of about 0.01 mg/l, gibberellic acid at a concentration of about 1 mg/l, and a selection agent at a concentration greater than the concentration of the selection agent in the first selection medium. The choice and concentration of the selection agent will depend upon the selectable marker in the genetic construct. Kanamycin at a concentration of greater than 50 mg/l is a preferred selection agent for the second selection medium. Kanamycin at a concentration of about 100 mg/l is an especially preferred selection agent. Geneticin and neomycin are also suitable selection agents. The shoot elongation medium or second selection medium also preferably comprises Timentin at a concentration of about 250 mg/l. GUS staining of the stem segments of the shoots may also be monitored to eliminate chimeric shoots. This may be accomplished by taking cross sections of the basal regions of putative transformed shoots and staining overnight according to methods described in Stomp, "Histochemical Localization of β-Glucuronidase," GUS Protocols: Using the GUS gene as a reporter of Gene Expression, 103–113, 1992. To ensure chimera-free transgenic plants, only the shoots showing 100% GUS staining may be selected for plantlet development.

Transformed shoots are transferred to a suitable rooting medium. A preferred rooting medium comprises Gamborg medium (Sigma G5893) or Knop medium (Knop, W., Untersuchungen uber den Ernahrungsprozess der Pflanzen, Landw Versuchs. Stat. 7:93–107, 1865) comprising IBA at a concentration of about 1 mg/l, a selection agent such as kanamycin at a concentration of about 100 mg/l, and timentin at a concentration of about 250 mg/l. Rooting is accomplished in a period of from about two to four weeks and may involve an initial culture period in the dark to allow initial root development, followed by transfer to standard photoperiod conditions. During elongation and rooting, explants may be transferred to larger culture vessels, such as Magenta boxes. Rooted shoots, or plantlets, may be transferred to a growth medium and grown to mature, genetically modified plants. Genetically modified plants produced according to the methods disclosed herein may be reproduced, for example, using standard clonal propagation techniques such as axillary bud multiplication techniques.

The following examples are offered by way of illustration and not by way of limitation. The examples describe experiments involving optimization of the regeneration and transformation protocols for Eucalyptus transformation. All refer to adventitious bud induction from stem segments obtained from in vitro micropropagated shoot cultures of *E. grandis* x *nitens* clone 910.59 (Fletcher Challenge Forests, New Zealand). The tissue culture conditions in all examples, unless otherwise noted, were: temperature 20° C.; 16 hour photoperiod; and cool white fluorescent lighting. These tissue culture conditions are generally preferred. All cultures were placed in 20×100 mm petri dishes, 10 stem segments per dish.

Plant Materials

All plant materials were provided by TeTeko laboratory, Fletcher Challenge Forest Col, New Zealand. *E. grandis* X *E. nitens* clones 910.59, 910.62 and 910.64 were obtained as in vitro microprogated shoot cultures grown on a multiplicaiton medium (full strength MS medium, sucrose 30 g/l, BA 0.1 mg/l, and NAA 0.01 mg/l) for 3 weeks, and then transferred to elongation medium (full strength MS medium, sucrose 30 g/l, BA 0.1 mg/l, NAA 0.01 mg/l and gibberellic acid 1 mg/l) for 4 to 6 weeks.

Agrobacterium Construct

The construction of the binary vector pKIWI is described by Janssen and Garner in Plant Molecular Biology 14:61–72, 1989. This construct contains a chimeric gene, which expresses β-D-glucuronidase (GUS) in transformed plant tissues but not in bacterial cells, since the GUS gene lacks a bacterial ribosome-binding site. Binary plasmid vector pKIWI 105 was transformed into Agrobacterium tumefaciens strain AGLI (Bio/Technology 9:963–967, 1991) by the freeze thaw method described in An G., Elbert P., Mitra A., and Ha S., "Binary Vectors," in: Gelvin SB, Schilperoorth RA (eds), Plant Molecular Biology Manual, pp. A3/1–A3/19, Dordrecht: Kluwer Academic Publishers, 1988.

Preparation of Agrobacterium for Transformation

Colonies of Agrobacterium strain AGLI carrying pKIWI 105 were grown on YEP medium (yeast 20 g, peptone 20 g, NaCl 10 g) for 2–3 days. A single colony from the plate was selected and grown in culture tube containing 5 ml of YEP medium with kanamycin 100 mg/l and rifampicin 50 mg/l. Cultures were incubated at 29° C. with vigorous shaking. The overnight Agrobacterium culture was centrifuged at 3000 g for 20 minutes and resuspended with YEP, then washed 3 more times. The cells were resuspended in 1/10 sterile MS medium with the addition of 50 μM acetosyringone and the $OD_{600}$ of the inoculum was adjusted to around 0.15. Cultures were allowed to grow on a shaker for 3 to 4 hours at 29° C. before inoculation.

Preparation of Plant Materials for Transformation

In vitro shoot cultures were subcultures in a multiplication medium (Full strength MS medium, sucrose at 30 g/l, BA at 0.1 mg/l, and NAA at 0.1 mg/l) for 3 weeks, and then transferred to shoot elongation medium (full strength MS medium, sucrose 30g/l, BA 0.1 mg/l, NAA0.01 mg/l and gibberellic acid 1 mg/l) for 4 to 6 weeks. All cultures were transferred to fresh medium 2–3 weeks before transformation.

Mature shoots of 34 cm were chosen. To maximize adventitious bud induction, only stem segments from the second and third nodes were used. All leaves were peeled and discarded. Additional wounding was achieved by light longitudinal cutting of both sides of the stem with a scalpel blade. Second and third nodes of the shoots were carefully excised and placed in a flask containing the Agrobacterium suspension.

Inoculation of Explants with Agrobacterium and Regeneration of Putative Transgenic Shoots Stem segments were incubated with the Agrobacterium suspension, prepared as described above, for 30 minutes on a shaker at 100 rpm at 20° C. After incubation, excess suspension was blotted with sterile tissue papers, stem segments were then transferred to a co-cultivation medium (MS medium with 0.4% glucose). All explants were placed horizontally onto the surface of the medium during the 3 day co-cultivation period. After co-cultivation, all stem segments were removed from the medium, washed with MS medium containing 250 gm/l timentin 3 times for 5 minutes each. After washing, stem segments were cultured vertically in selection medium (MS+3% sucrose+cytokinin and auxin+timentin 250 mg/l+kanamycin 50 mg/l). In addition to kanamycin, selection of transformed tissues may be carried out using G-418, which is also known as geneticin or neomycin. Other selection agents corresponding to a selectable marker in the expression vector may also be used. Subculture of stem segments onto fresh medium was done every week for the first 4 weeks until adventitious buds were produced from the stem segments.

Selection of Stably Transformed Shoots

Putative transformed adventitious shoots were excised from the stem segments. All shoots were transferred to shoot elongation medium (MS medium, sucrose 30 g/l, BA 0.1 mg/l, NAA 0.01 mg/l, gibberellic acid 1 mg/l, kanamycin 100 mg/l, timentin 250 mg/l) for 2 to 4 weeks. This second step of selection medium with a higher kanamycin concentration was included to further eliminate chimeric shoots which might have escaped from the first, lower kanamycin selection process. GUS staining of the stem segments of the shoots was monitored to further eliminate chimeric shoots. This was done by taking cross sections of the basal regions of all putative transformed shoots and staining overnight with GUS (Histochemical localization of β-glucuronidase. GUS Protocols: Using the GUS gene as a reporter of gene expression Pg. 103–113, 1992). Careful analysis of the GUS distribution patterns of the stem sections reveals shoots which are stably transformed (whole stem sections are stained blue) versus those which are partially blue, and those with no staining at all. To ensure 100% chimera-free transgenic plants, only those shoots which showed 100% GUS staining were selected for plantlet development.

EXAMPLE 1

This experiment was designed to determine the best age of stem segments for adventitious bud induction. The basal medium used was full-strength Murashige and Skoog (MS) medium (Sigma M5519) and sucrose 30 g/L. The age of stem segments (apical, 1st, 2nd, 3rd and 4th nodes) were tested in combination with the concentrations of Benzylaminopurine (BA—1, 2 and 3 mg/L). All media contained Napthalene acetic acid (NAA) at 0.01 mg/L.

In vitro shoots of 3–4 cm were cut into single node segments. The leaves were removed prior to culture. Approximately twenty explants were cultured for each treatment. Cultures were transferred to fresh media every 3 weeks. Adventitious bud development assessments were done after 5 weeks in culture. The percentages of explants forming adventitious shoots for each treatment are listed below.

| Age of Stem Segments | BA Concentration | | |
| --- | --- | --- | --- |
| | 1 mg/L | 2 mg/L | 3 mg/L |
| Apical Shoot Tips | 25% (5/20) | 5% (1/20) | 33% (7/20) |
| First Node | 57% (12/21) | 35% (7/20) | 20% (4/20) |
| Second Node | 76% (16/21) | 12% (6/20) | 20% (4/20) |
| Third Node | 75% (15/20) | 15% (3/20) | 15% (3/20) |
| Fourth Node | 45% (9/20) | 38% (8/21) | 10% (2/20) |

To maximize the number of adventitious buds induced from stem segments, only the 2nd and 3rd node segments were cultured on MS medium containing 30 g/L sucrose, 1 mg/L BA and 0.01 mg/L NAA for 4 weeks in subsequent transformation experiments.

EXAMPLE 2

This experiment was designed to determine the optimal concentration of kanamycin to be used for selection of transformed bud tissues. Explants were cultured as described at the end of Example 1, in combination with kanamycin levels of 0, 5, 10, 25, 50 or 100 mg/L. In vitro shoots of 3–4 cm in size were cut into single node segments, and the appropriate segments used. All leaves were removed prior to culture. Approximately thirty explants were used for each treatment. Cultures were transferred to medium after 3 weeks in culture, and the percentage of bud inhibition determined after 5 weeks in culture.

| Kanamycin Concentration | % of Stem Segments Forming Adventitious Buds | % Bud Inhibition Relative To Control |
|---|---|---|
| 0 mg/L | 80% (24/30) | 0% |
| 5 mg/L | 64% (18/28) | 20% |
| 10 mg/L | 47% (14/30) | 41% |
| 25 mg/L | 33% (10/30) | 59% |
| 50 mg/L | 15% (14/31) | 81% |
| 100 mg/L | 3% (1/30) | 96% |

The highest degree of bud inhibition was found using 100 mg/L kanamycin. A lower level of selection will (25–50 mg/L) be used for the initial selection of taansformed adventitious buds. For the effective selection against chimeric shoots, 100 mg/L kanamycin will be used for the subsequent selection of transformed shoots.

EXAMPLE 3

This experiment was designed to determine if a cytokinin pretreatment of stem segments prior to Agrobacterinm infection improved the tranformation efficiency. Second and third node segments were precultured on bud induction medium (MS medium containing 30 g/L sucrose, 1 mg/L BA and 0.01 mg/L NAA) for 0, 1, 2, 4 or 7 days prior to Agrobacterium infection.

In vitro shoots of 3–4 cm in size were cut into into single node segments. A minimum of 50 nodal segments (2nd and 3rd nodes) were used for each treatment. Cultures were transferred to fresh media every 3 weeks. All tissues were stained to detect GUS activity (Histochemical localization of ($\beta$-glucuronidase. GUS Protocols: Using the GUS gene as a reporter of gene expression. Pg. 103–113) as an indication of transformation.

| Duration of Cytokinin Pretreatment | % of Total Explants GUS Positive | % of Total Explants GUS Positive in Buds |
|---|---|---|
| 0 Days | 9% (10/109) | 4% (4/109) |
| 1 Day | 3% (2/73) | 0% |
| 3 Days | 5% (3/60) | 0% |
| 4 Days | 5% (3/60) | 0% |
| 7 Days | 4% (2/53) | 0% |

The above results indicated that preculture of explants with cytokinin did not improve the transformation efficiency. In fact, explants turned brown following Agrobacterium infection. For all subsequent transformation experiments, stem segments were infected with Agrobacterium immediately after excision.

EXAMPLE 4

The preferred transformation and regeneration protocol, based on the previous Examples and the disclosure made herein, is as follows.
Preparation of in vitro Micropropagated Stocks:
Regular subculture of shoots in elongation medium every 3–4 weeks.
Duration=3–4 weeks
Preparation of Agrobacterium for Transformation:
Prepare fresh Agrobacterium cultures, centrifuge overnight culture and grow in 1/10 strength sterile MS medium, with the addition of 50 (M acetosyringone for 3–4 hours to an $OD_{600}$ of 0.3–0.5.
Duration=2 days.
Preparation of Plant Materials for Tranformation:
Select elongated shoots of 3–4 cm in height, growing in a shoot elongation medium (MS medium containing 30 g/L sucrose, 0.1 mg/L BA, 0.01 mg/L NAA and 1 mg/L Gibberellic acid=GA3)
Duration=continual
Inoculation of Explants with Agrobacterium:
Incubate stem segments with Agrobacterium suspension for 30 minutes on a shaker (100 rpm) at 2° C. Transfer stem segments to a co-cultivation medium.
Duration=3 days.
Induction of Putative Transformed Adventitious Buds:
Wash explants 3×5 minutes with MS medium containing 250 mg/L timentin on shaker. After washing, culture stem segments in bud induction/selection medium (MS medium containing 30 g/L sucrose, 1 mg/L BA, 0.01 mg/L NAA, 50 mg/L kanamycin and 250 mg/L timentin). Subculture to fresh medium weekly.
Duration=3–4 weeks.
Regeneration of Putative Transgenic Shoots:
Excise all putative transformed adventitious shoots and transfer to shoot elongation medium (MS medium containing 30 g/L sucrose, 0.1 mg/L BA, 0.01 mg/L NAA, 1 mg/L GA3, 100 mg/L kanamycin and 250 mg/L timentin).
Duration=4–6 weeks.
Production of Transgenic Plants:
Select all GUS positive shoots and transfer to rooting medium (Gamborg or Knop medium containing 1 mg/L Indole-3-butyric acid=IBA, 100 mg/L kanamycin and 250 mg/L timentin)
Duration=2–4 weeks)
The total duration of transformation and regeneration procedure is about 10–15 weeks.

While the methods of the present invention have been described with reference to certain preferred embodiments thereof, it will be recognized that additional methods, configurations, embodiments and arrangements may be used without departing from the invention.

I claim:

1. A method for producing genetically modified plant material comprising:
    preparing an in vitro shoot culture of a target plant, the target plant being of the Eucalyptus or Pinus species;
    maintaining and growing the shoot culture until it has produced multiple modes and stem segments;
    selecting and excising the stem segments from one or more nodes of a shoot;
    transforming a stem segment by stably incorporating a genetic contruct comprising a selection marker and a polynucleotide of interest into the stem segment to form a putatively transformed stem segment;
    exposing a putatively transformed stem segment to a selection medium comprising a selection agent that permits survival of transformed stem segments and is lethal to stem bud on the that were not successfully transformed;
    selectively inducing the formation of an adventitious bud on the putatively transformed stem segment to form a putatively transformed adventitious bud;
    selectively regenerating the putatively transformed adventitious bud by excising the putatively transformed adventitious bud and exposing the putatively transformed adventitious bud to a selection medium comprising a selection agent that permits survival of transformed adventitious buds and is lethal to adventitious buds that were not successfully transformed to identify a transformed adventitious bud; and elongating the transformed adventitious bud to form a transformed shoot.

2. A method according to claim 1, wherein the genetic construct comprises a reporter gene and a polynucleotide desired to be introduced into the target plant.

3. A method according to claim 1, wherein the stem segments are from micropropagated shoot cultures.

4. A method according to claim 1, wherein the target plant stem segments are pretreated in a multiplication medium and then transferred to a shoot elongation medium.

5. A method according to claim 1, wherein transforming the stem segment comprises incubating the stem segment with an Agrobacterium culture transformed with the genetic construct.

6. A method according to claim 5, wherein the stem segments are wounded prior to incubation with the Agrobactefium culture.

7. A method according to claim 1, additionally comprising selecting transformed stem segments by exposing the putatively transformed stem segments to a first selection medium having a first concentration of a selection agent and subsequently exposing the putatively transformed stem segments surviving exposure to the first selection medium to a second selection medium having a second concentration of a selection agent greater than the first concentration.

8. A method according to claim 1, wherein the selection medium comprises kanamycin.

9. A method according to claim 7, wherein the first selection medium has a concentration of kanamycin less than or equal to 50 mg/l, and the second selection medium has a concentration of kanamycin greater than 50 mg/l.

10. A method according to claim 1, wherein the genetic construct comprises genetic material that is homologous to the genome of the target plant.

11. A method according to claim 1, wherein the genetic construct comprises genetic material that is heterologous to the genome of the target plant.

12. A method according to claim 1, wherein the genetic construct comprises genetic material that affects one of the following phenotypic properties of the target plant: insect tolerance; disease resistance; herbicide tolerance; sterility; rooting ability;

temperature tolerance; drought tolerance; salinity tolerance; wood properties; and growth rates.

13. A method according to claim 1, wherein the genetic construct comprises genetic material encoding a polypeptide of interest or a functional portion of a polypeptide of interest.

14. A method according to claim 1, additionally comprising transferring the transformed shoot to a rooting medium and forming a transformed plantlet.

15. A method according to claim 14, additionally comprising transferring the transformed plantlet to a planting medium and growing the transformed plantlet to form a mature, genetically modified plant.

16. A method according to claim 1, wherein the selected and excised stem segments from one or more nodes of a shoot comprise second or third nodes of the stem segments.

* * * * *